(12) United States Patent
Potts et al.

(10) Patent No.: US 7,591,074 B1
(45) Date of Patent: Sep. 22, 2009

(54) MEDICAL LASER VERTICAL ALIGNMENT SYSTEM

(76) Inventors: Richard Allen Potts, 13719 8th Ave. SW., Burien, WA (US) 98166; Larry Ray Potts, 4742 N. Oberlin St., Portland, OR (US) 97203

( * ) Notice: Subject to any disclaimer, the term of this patent is extended or adjusted under 35 U.S.C. 154(b) by 0 days.

(21) Appl. No.: 12/321,408

(22) Filed: Jan. 20, 2009

(51) Int. Cl.
*A61B 5/02* (2006.01)
(52) U.S. Cl. ............. 33/290; 33/DIG. 21; 600/485
(58) Field of Classification Search ............ 33/290, 33/DIG. 21, 379; 600/485–488; 73/720–721, 73/717, 726, 727
See application file for complete search history.

(56) References Cited

U.S. PATENT DOCUMENTS

| | | | | |
|---|---|---|---|---|
| 3,590,818 A | * | 7/1971 | Lemole | 600/487 |
| 4,691,710 A | * | 9/1987 | Dickens et al. | 600/486 |
| 4,776,343 A | * | 10/1988 | Hubbard et al. | 600/488 |
| 5,168,633 A | * | 12/1992 | Harrison et al. | 600/486 |
| 5,280,789 A | * | 1/1994 | Potts | 600/486 |
| 5,691,478 A | * | 11/1997 | Barry et al. | 600/485 |
| 5,752,520 A | * | 5/1998 | Bisnaire et al. | 600/561 |
| 5,758,657 A | * | 6/1998 | MacEachern | 33/379 |
| 5,769,083 A | * | 6/1998 | MacEachern | 600/486 |
| 5,788,641 A | * | 8/1998 | Policastro et al. | 600/485 |
| 6,071,243 A | * | 6/2000 | MacEachern | 600/486 |
| 7,354,431 B2 | * | 4/2008 | Wilson | 600/561 |

* cited by examiner

*Primary Examiner*—Yaritza Guadalupe-McCall
(74) *Attorney, Agent, or Firm*—Mark S. Hubert

(57) ABSTRACT

A medical laser vertical alignment system that has a precise locating strip affixed perpendicularly to a static pressure scale and that vertically and horizontally aligns the center of rotation of a reusable detachable laser aligning device with the zero reference point of the scale. The laser beam light is adjustable to coincide with the indicated horizontal position of a set of two bubble leveling vials. It has a quick release and alignment clamping arrangement that affixes the laser aligning device to the locating strip. The leveling device can be rotated 180 degrees and the leveling vials are located at opposing sides and ends of the device for clear visibility and redundancy. There is a timer circuit in the device that shuts the laser off after a predetermined time.

10 Claims, 10 Drawing Sheets

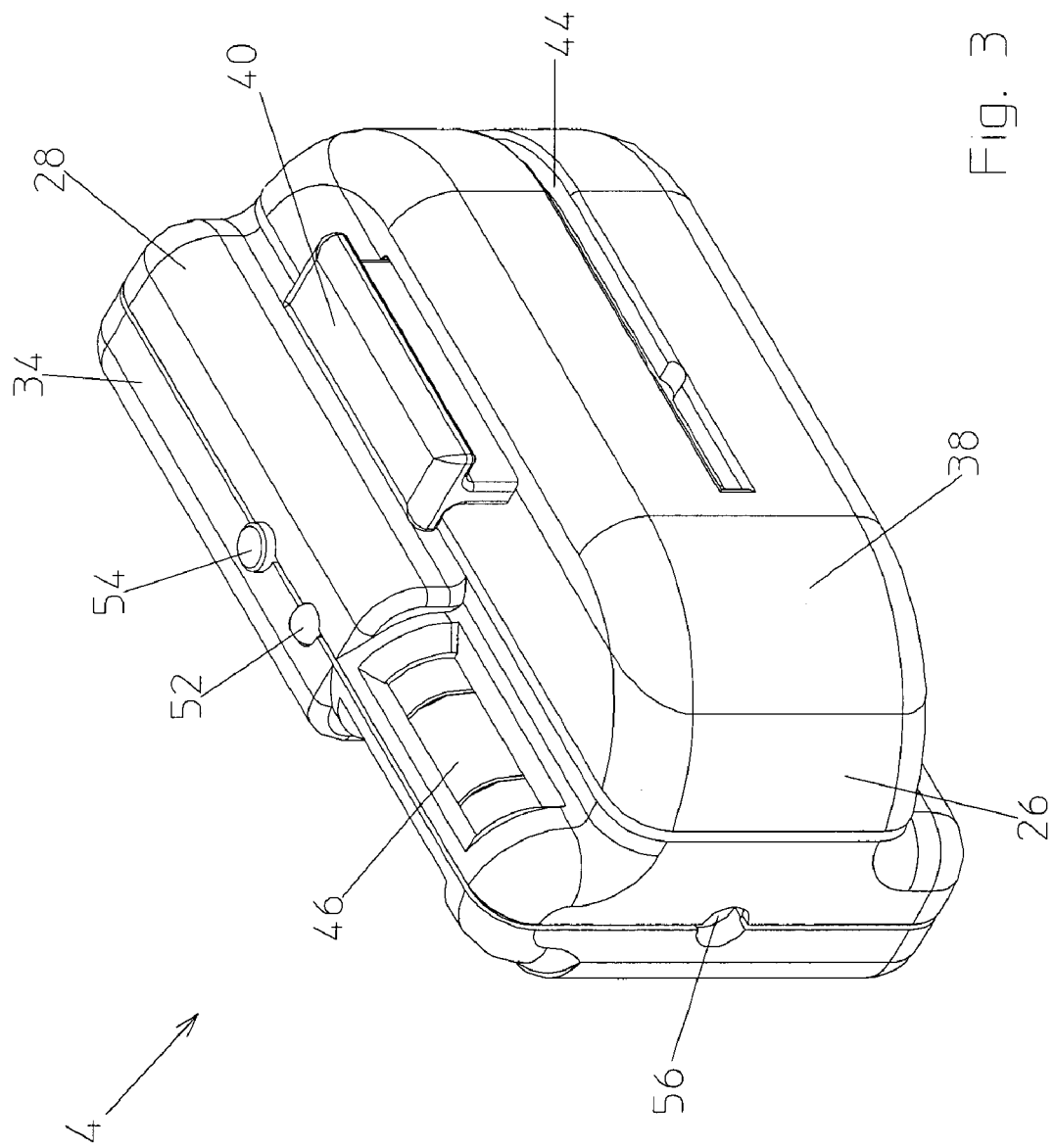

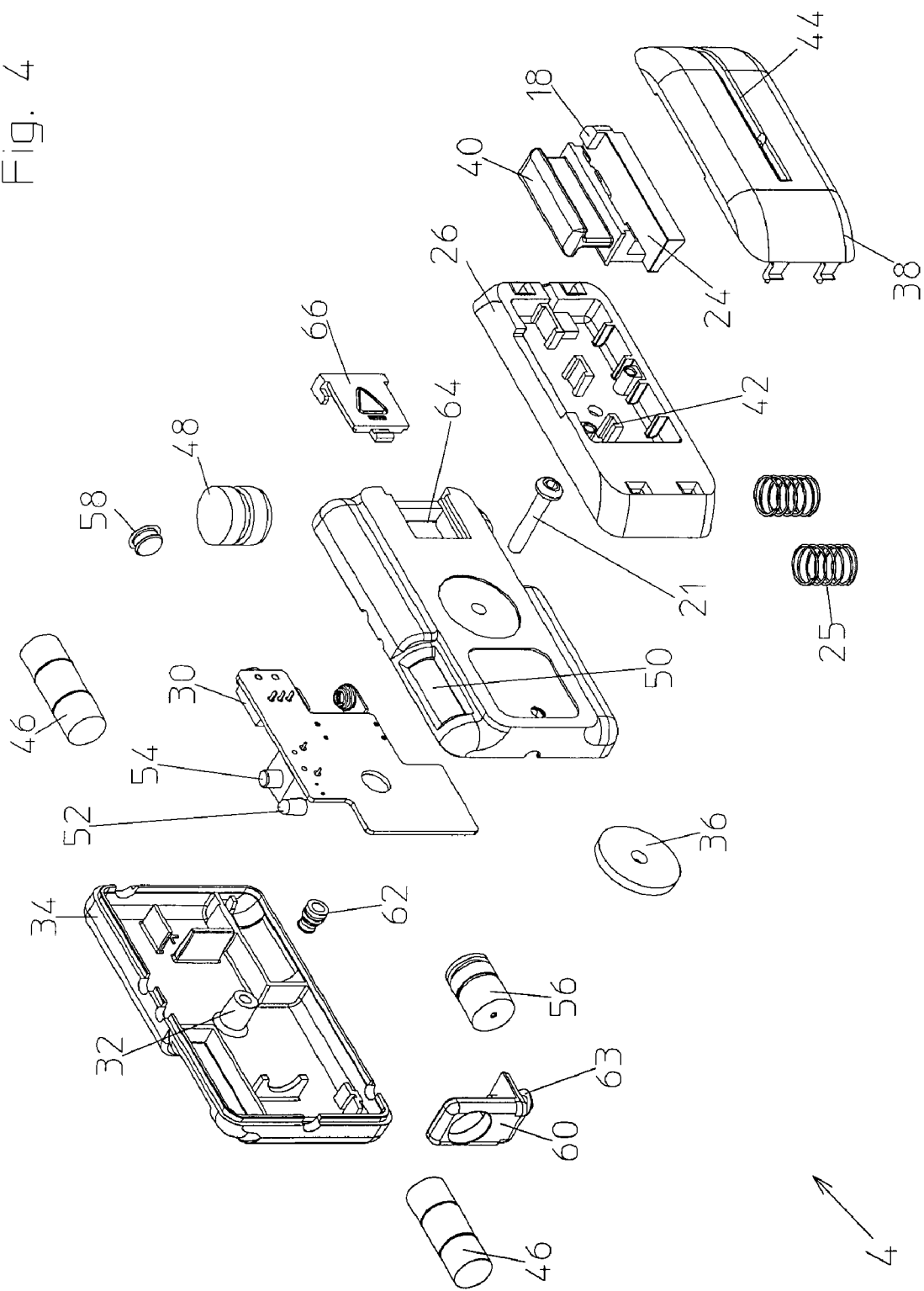

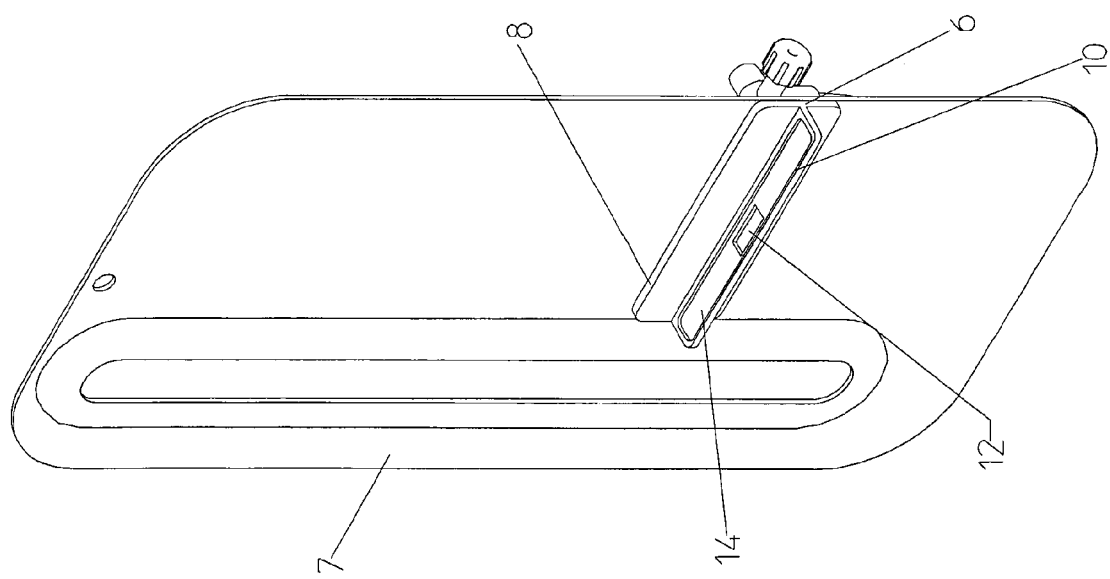

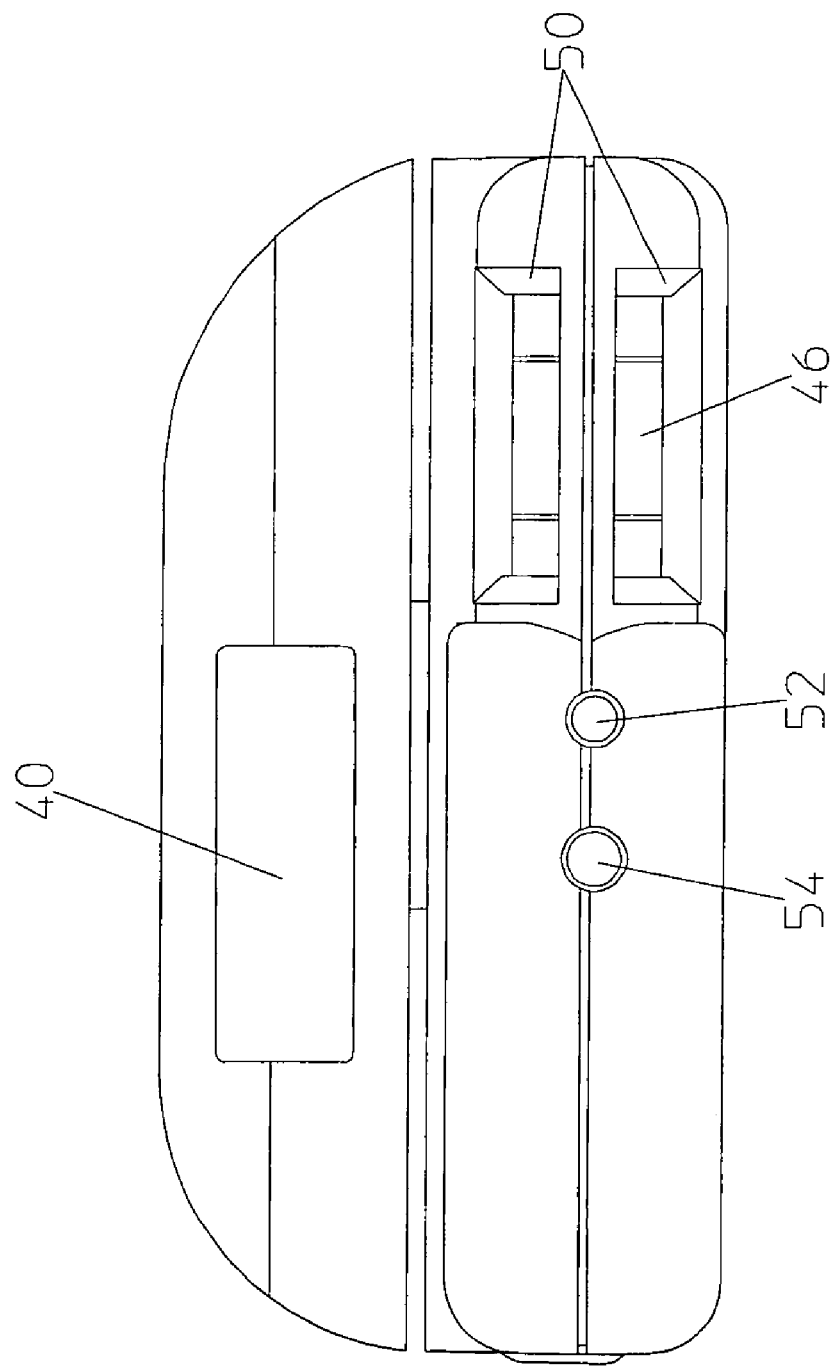

MEDICAL LASER VERTICAL ALIGNMENT SYSTEM

BACKGROUND OF THE INVENTION

The present invention relates to a laser alignment system for the precise vertical positioning of the static pressure scale of a medical personal drip or drain device. More particularly, to a reusable detachable laser aligning device that releaseably, and rotatably attaches to a locating strip mounted to the back of a static pressure scale and provides a laser beam that may be horizontally leveled and indicated onto the insertion point of a patient's catheter.

In many medical procedures a catheter connected to either a drainage bag or a drip bag is inserted into an opening in the human body for the pressure monitoring, addition or removal of fluids. This is commonly done in the patient's intracranial, intravascular, intracardiac, intrapulmonary or intrafascial compartments. The pressure at the point of the opening is often critical, as the differential pressure between this and the fluid level in the bag is the motive force for the movement of the fluids. For this fluid movement to be accomplished at a controlled rate, the differential pressure between the insertion point and the bag's fluid level must be accurately known. This requires that a precise vertical alignment of the "zero point" on the static pressure scale of the bag be made. This is accomplished through the vertical alignment of a horizontal laser beam with the insertion point of the catheter.

Prior art laser alignment systems exist but have many downfalls. Their leveling systems are not designed to be used on either side of the patient; their laser axis is not perfectly aligned with the zero reference point of their vertical static pressure scale; they have a single leveling indicator; they do not have adjustment means to level the laser light beam with the leveling indicator; visibility of the leveling indicator is poor; and they do not have a system for rapid alignment of the laser's axis with the zero reference point.

The present invention includes a precise locating strip affixed perpendicularly to a static pressure scale that vertically and horizontally aligns the center of rotation of a reusable detachable laser aligning device with the zero reference point of the scale. The laser is adjustable to coincide with the indicated horizontal position of both vials in a set of bubble leveling vials. The leveling device has a quick release and alignment clamping arrangement. The leveling device can be rotated 180 degrees for use on either side of the patient and the leveling vials are located at opposing sides and ends of the device for clear visibility and redundancy. There is a timer circuit in the device that shuts the laser off after a predetermined time to ensure maximum battery life and to allow a hands off setup.

Henceforth, such a medical laser alignment system with the described advantages would fulfill a long felt need in the medical industry. This new invention utilizes and combines known and new technologies in a unique and novel configuration to overcome the aforementioned problems and accomplish this.

SUMMARY OF THE INVENTION

The general purpose of the present invention, which will be described subsequently in greater detail, is to provide a system for the precise alignment of a static pressure scale for a medical drip/drain system to the patient's point of body injection.

It has many of the advantages mentioned heretofore and many novel features that result in a new medical laser alignment system which is not anticipated, rendered obvious, suggested, or even implied by any of the prior art, either alone or in any combination thereof.

In accordance with the invention, an object of the present invention is to provide an improved medical laser alignment system capable of detachment and reuse on disposable medical drain/drip systems.

It is another object of this invention to provide an improved medical laser alignment system capable of bidirectional horizontal indication by rotation of the laser about a pivot point.

It is a further object of this invention to provide a medical laser alignment system that orientates its horizontal axis of illumination to the zero reference point of a vertical static pressure scale.

It is still a further object of this invention to provide for a rotatable medical laser alignment system that orientates its pivot point to the zero reference point of a vertical static pressure scale.

It is yet a further object of this invention to provide a medical laser alignment system that has a pair of bidirectional leveling means for horizontal leveling of the axis of illumination.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

FIG. 3 is a perspective view of the vertical alignment laser;

FIG. 4 is an exploded view of vertical alignment laser showing the general arrangement of all components;

FIG. 5 is a perspective view of the vertical alignment tab on a vertical graduated scale;

FIG. 6 is a top view of the vertical alignment laser;

DETAILED DESCRIPTION

Figure 2:
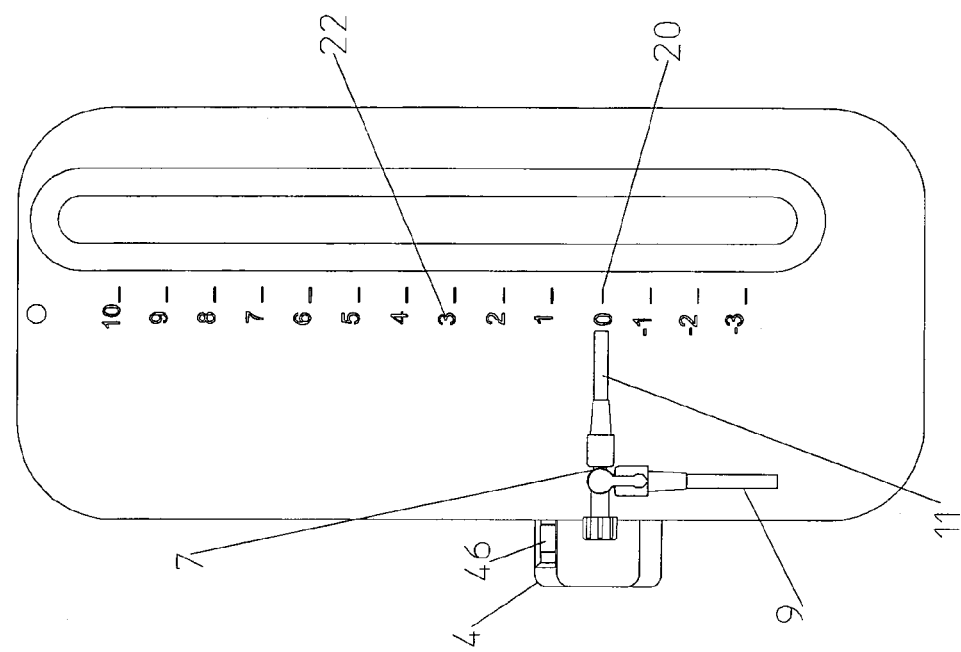
FIG. 2 is a rear view of the laser vertical alignment system attached to a medical pressure scale.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

The medical industry commonly utilizes a rigid substrate with a vertical graduated scale and a catheter vessel (a tube, bag, bladder, or tubing) residing adjacent the scale. Referencing of the fluid level in the vessel to the indicated scale gives the viewer the precise indication of what the static pressure is at the catheter. Since this pressure is used to determine the amount of push or drainage at the catheter insertion point, it is desirable to have the zero point of the graduated scale set to the same vertical elevation as the catheter. In this way a positive pressure indicates fluid is being pushed into the patient and a negative pressure indicates the fluid is being drained from the patient. For the scale to show the precise relative magnitude of static pressure the zero point must be correctly set. This device provides for a simple method of aligning the zero point of the scale with the catheter insertion point through the use of a horizontal laser beam directed from the zero point of the graduated scale to the catheter.

Figure 1:
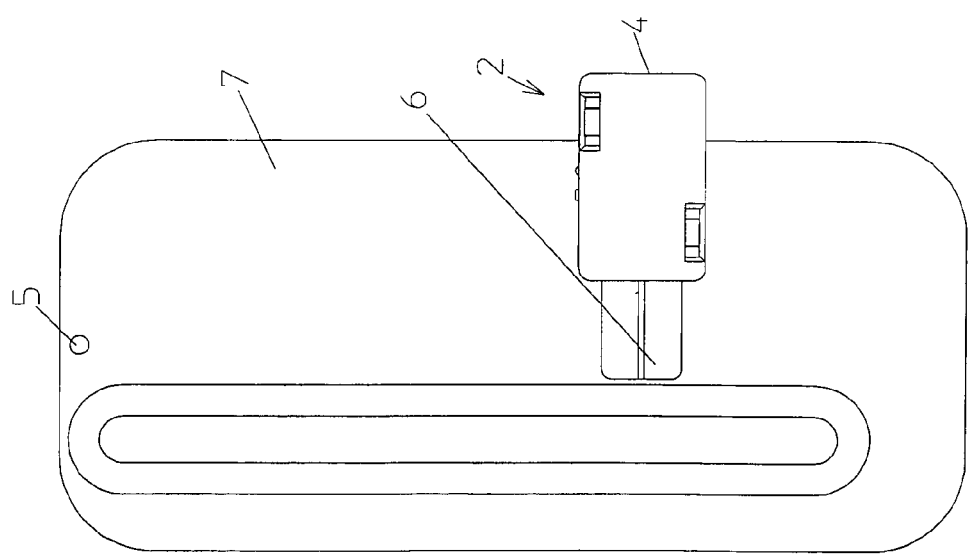
FIG. 1 is a front view of the laser vertical alignment system attached to a medical pressure scale.

Looking at FIG. 1 it can be seen that the laser vertical alignment system 2 is made up of a vertical alignment laser device 4 and a vertical alignment tab 6. The tab 6 is rigidly affixed to the surface of a rigid substrate 7 with a vertical graduated scale 22 affixed thereon. The vertical scale 22 has a zero point 20 indicated thereon. The substrate 7 may be hung from a pole stand by rope passing through a hanging orifice 5 formed through the substrate 7 or it may be rigidly attached to a pole stand by a side clamp (not illustrated.) The tab 6 is affixed such that its linear axis resides perpendicular to the axis of the vertical scale, and is aligned with the zero reference point 20 of the scale 22. Looking at FIG. 5 the configuration of the tab 6 can best be seen. Tab 6 is made of an alignment strip 10 that extends normally from the centerline of mounting plate 8 such that their respective linear axes are parallel. Both components of the tab 6 are made from a rigid planar substrate. The alignment strip 10 has a linear depression or channel 14 formed thereon with an alignment orifice 12 formed there through. The linear depression 14 and alignment orifice 12 are matingly conformed to receive a stabilizing bar 24 and locating tab 18 (FIG. 4) on the laser device 4 which will be discussed in detail herein. The mounting plate 8 is designed for mechanical or chemical attachment to the surface of the rigid substrate 7.

FIG. 2 illustrates the back view of the device 2 affixed to substrate 7 wherein the bubble level vial 46 can readily be viewed. The drain tube 9 and feed tube 11 connect to their respective vessels that are located at an elevation to achieve the desired flows.

Looking at FIG. 4 the components of the laser device 4 can be seen in an exploded view. The laser device 4 is made of two pivotally connected bodies, each having separate but integral functions for the overall operation of the laser device 4. The scale alignment body and the laser body are pivotally connected by a pivot screw 21 that passes sequentially through aligned orifices formed through the scale alignment body back casing 26, polymer pivot disk 36, the laser body back casing 28, the printed circuit board (CB) 30 and threadingly engages into a screw insert 62 that is pressed into post 32 heat staked onto the laser body front casing 34. The linear axis of this pivot screw 21 coincides with the midpoint of the scale alignment body and the laser body. The friction between the faces of the pivot disk 36, the scale alignment back casing 26, and the laser body back casing 28 is strong enough to prevent the relative movement of either body without an external force. The polymer pivot disk 36 is of a resilient, smooth friction reducing material such as HDPE. Optionally locking style washers may also be included in this arrangement.

The scale alignment body has a depressable stabilizing bar 24 that is encased between the scale alignment back casing 26 and the scale alignment front casing 38. A set of two compressed springs 25 reside beneath the stabilizing bar 24 and within the scale alignment body 24 exerting an upward pressure so as to force the stabilizing bar's button 40 to sit an operable amount above the assembled casing halves. A series of movement guides 42 ensure that the stabilizing bar 24 can only experience motion along the axis of compression. The scale alignment front casing 38 has a longitudinal slot 44 extending from one edge across much of its length. The stabilizing bar 24 resides directly behind and adjacent the slot 44 such that their linear axes are aligned and the stabilizing bar 24 blocks the slot 44.

In operation, the stabilizing bar's button 40 is depressed, thereby compressing the springs 25 and allowing the stabilizing bar 24 with its locating tab 18 to move below longitudinal slot 44. With the slot 44 exposed, the alignment strip 10 may be slid into and along the slot 44 until an abutment occurs with the end of the slot 44. The button 40 is released causing the springs 25 to force the stabilizing bar 24 upward and into contact with the alignment strip 10. Here, since the linear depression 14 and alignment orifice 12 on one side of the alignment strip 10 are matingly conformed to receive the stabilizing bar 24 and locating tab 18, the scale alignment body of the laser device 4 is now locked onto the substrate 7 so as to reside perpendicular to the vertical axis of the graduated scale 22 and with the slot 44, the stabilizing bar 24 and the pivot screw 21 in vertical alignment with the zero point 20. With the stabilizing bar 24 locked into one side of the alignment strip 10, the opposite side of the alignment strip 10 is also frictionally engaged against the longitudinal slot 44 by the force exerted on the stabilizing bar 24 by springs 25. When the stabilizing bar 24 and locking tab 18 is engaged onto the alignment strip 10 the laser device 4 cannot move in the X, Y or Z axis with respect to the substrate 7.

The laser body is made of the following components: two bubble level vials 46; a DC battery power source 48; a PCB 30 with a timer circuit, timer light 52, laser activation button 54, laser circuit and laser 56; an AC input jack 58 (FIG. 3); a laser adjustment plate 60; a screw insert 62, and a laser alignment screw 63 (FIG. 7) that are encased between a back casing 28 and a front casing 34 with various posts 32 formed thereon. The two casing halves each have top and bottom bubble level cutouts 50 and a battery compartment 64 and battery compartment door 66 as well.

Figure 7:
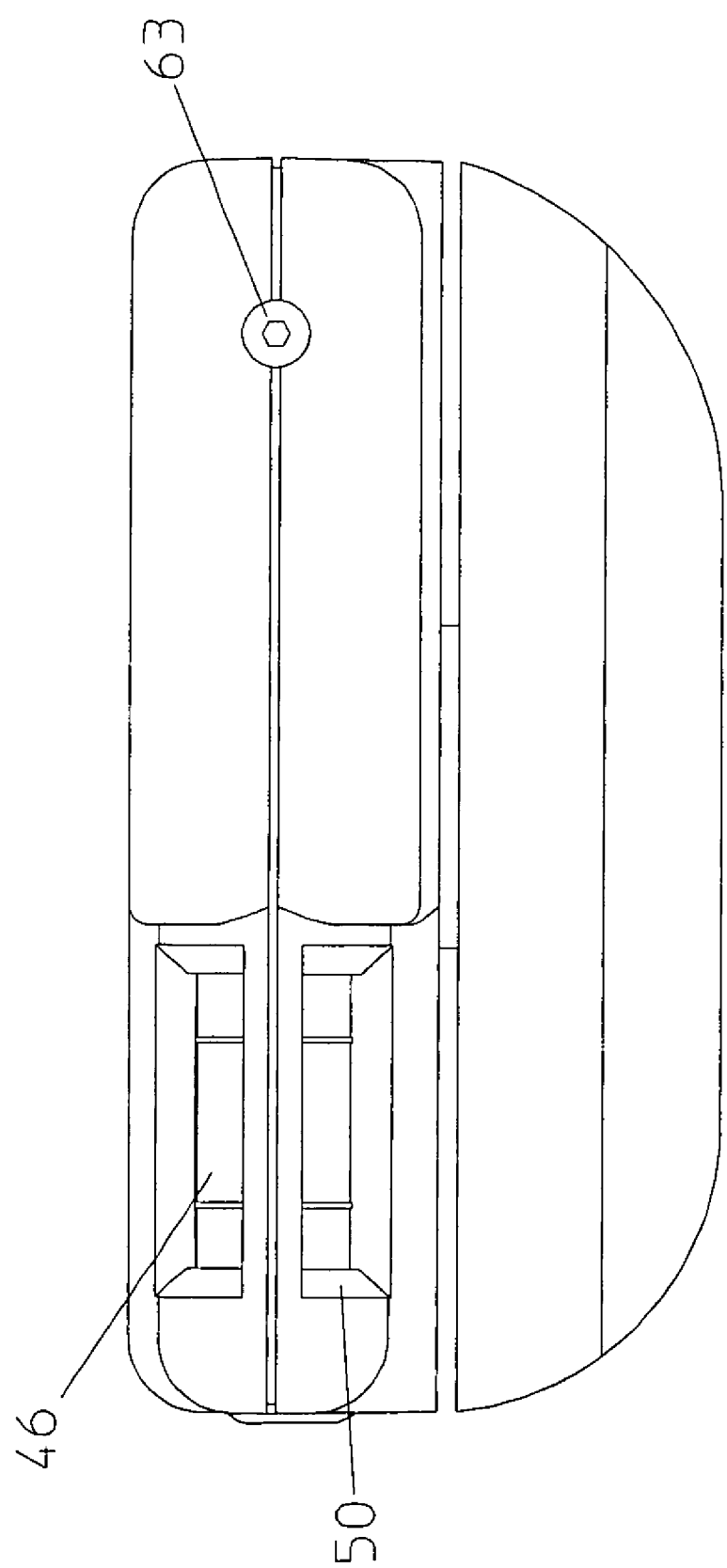
FIG. 7 is a bottom view of the vertical alignment laser.
Figure 8:
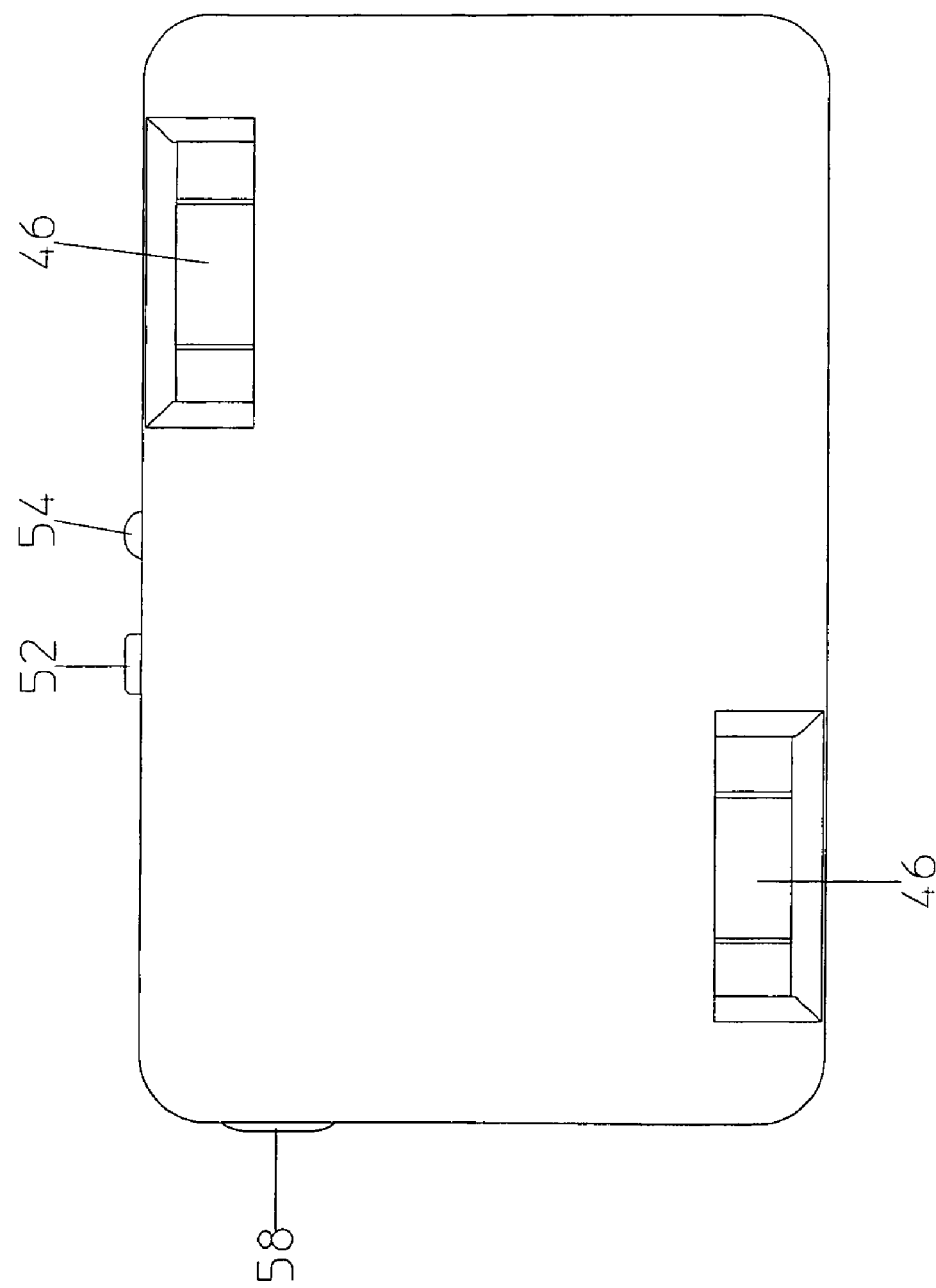
FIG. 8 is a front view of the vertical alignment laser.

Looking at FIGS. 6, 7 and 8 it can be seen that back casing 28 and front casing 34 each have identical bubble level cutouts 50 between which the bubble level vials 46 can be seen. This feature allows for horizontal leveling and level checking of the device from any side of the device. It also allows light to shine through the back of the level vials 46 which greatly enhances the distinction between the tinted liquid and the air bubble in the level vials 46. The cutouts 50 are located at diagonally opposite corners of the laser body, thus a level vial 46 is always located along the top horizontal surface of the laser body after any 180 degree rotation. Additionally the offset in the bubble vials allows for edge visibility.

The timing circuit allows the laser 56 and laser circuit to remain energized for a specified period of time after the laser activation button 54 is depressed. This accomplished two functions. First, it allows the user to adjust the vertical height of the substrate 7 (and thus the vertical laser light indication) on the pole with both hands and second, it prevents the batteries 48 from draining in the event the laser is inadvertently left on. In the preferred embodiment this time interval is 20 seconds.

Figure 9:
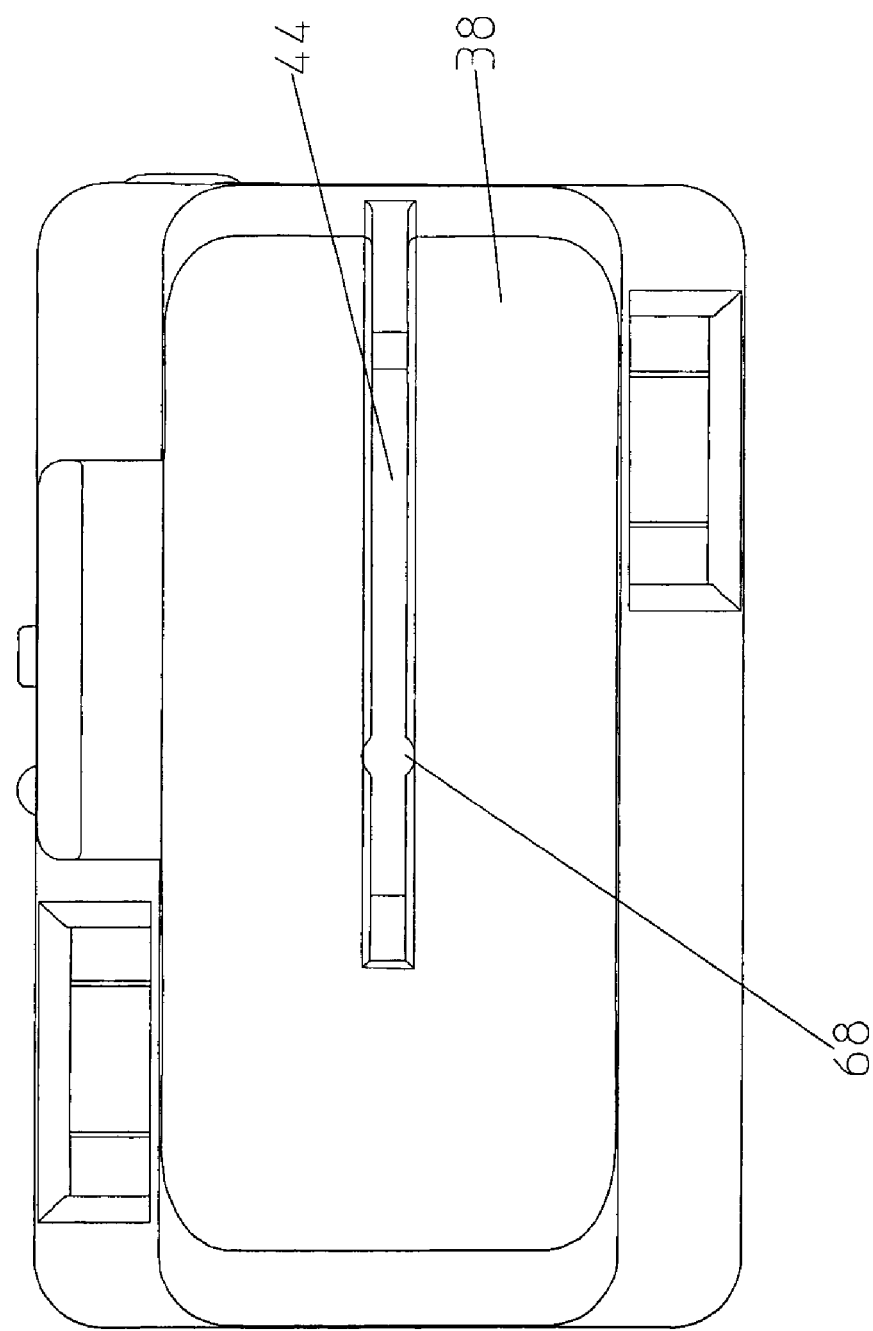
FIG. 9 is a back view of the of the vertical alignment laser.

Looking at FIG. 9 it can be seen that on scale alignment front casing 38 there is a screwdriver receiving widening 68 of the longitudinal slot 44 to allow access for the tightening of the pivot screw.

Figure 10:
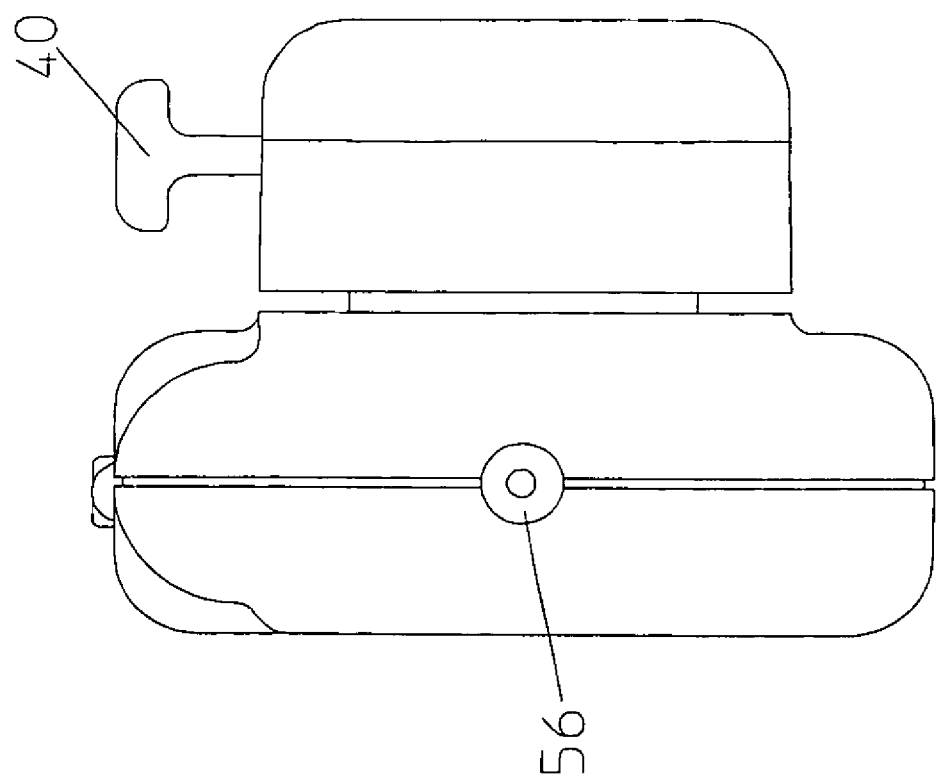
FIG. 10 is a laser end view of the vertical alignment laser.
Figure 11:
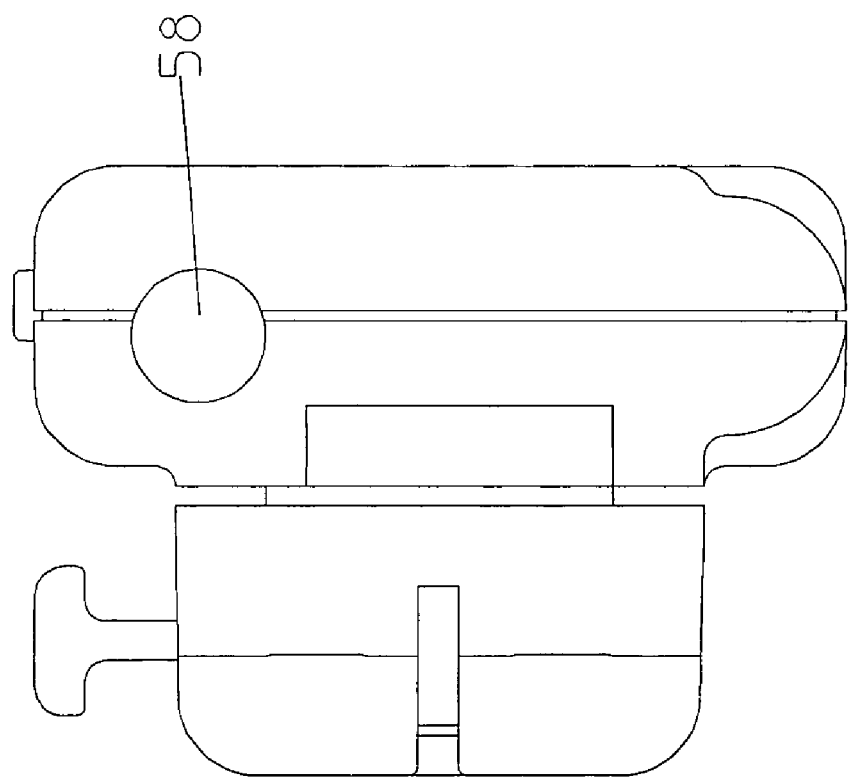
FIG. 11 is an end view of the vertical alignment laser.

FIG. 10 illustrates that the laser 56 is centrally located within the laser body thus when the laser body is horizontally aligned, the laser 54 is in direct alignment with the pivot screw 21 and the slot 44. Therefore when the vertical alignment laser device 4 is engaged with the vertical alignment tab on the surface of the rigid substrate 7, the source of the laser light is aligned vertically with the zero point 20 of the vertical scale 22. By virtue of the symmetrical design of the laser body, there would be no need to establish the alignment of the laser 56 to the zero point 20 when the laser body is rotated 180 degrees (as would be done in the situation where the pole and substrate 7 were to be moved to the opposite side of the patient.)

The laser device 4 is calibrated by placement of it onto a bench mounted horizontally positioned tab 6. The spring loaded stabilizing bar 24 is depressed, fit into the linear depression 14 and released such that the tab 6 is frictionally engaged between the stabilizing bar 24 and slot 44. The laser device 4 is then slid along the linear axis of the tab 6 until the locating tab 18 engages the alignment orifice 12. At this time the laser device 4 is wiggled to ensure that it is locked against any horizontal and vertical movement in all three axes, X, Y and Z. The bubbles in the level vials 46 are checked for alignment between the center lines. Since the device casings are precision cast the level vials 46 should indicate true horizontal unless the level vials 46 are flawed. If flawed, they are replaced. The laser activation button 54 is depressed and a laser light is momentarily projected toward a marked spot some distance away that corresponds to a laser that is parallel to the two level vials 46 and the axis of the tab 6. The laser is adjusted by twisting a laser alignment screw 63 so as to raise or lower laser adjustment plate 60 until the laser light resides within an acceptable distance of the marked spot. The laser device 4 is now aligned with the level vials 46 and ready for operation.

In operation, once aligned, the laser device 4 is attached to the alignment strip as detailed above. The laser body is pivoted slightly until the top level vial 46 has its bubble in the central, marked horizontal alignment region. The laser activation button 54 is depressed and a laser light is momentarily projected toward the catheter insertion point. The substrate 7 is raised or lowered until the laser light directly shines on the catheter insertion point. The zero reference point 20 of the vertical scale 22 is now calibrated to the static fluid pressure at the patient's catheter insertion point. Additional fluid vessels may be adjusted vertically on the pole or substrate 7 with respect to the zero reference point 20 to push fluid in or drain fluid from the patient at a known rate or with a known pressure. The positive engagement system between the vertical alignment laser device 4 and a vertical alignment tab 6 quickly and accurately positions the laser device's pivot point at the zero reference point 20 mid scale at a horizontal level position normal to the vertical scale 22.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A medical laser vertical alignment system comprising:
   a scale alignment body enclosed by a back casing and a front casing;
   a laser body enclosed by a back casing and a front casing;
   a pivot screw; and
   a pivot disk;
   wherein said scale alignment body's back casing resides adjacent to said laser body's back casing and said scale alignment body is rotatably connected to said laser body by said pivot screw that passes sequentially through a first orifice formed through said scale alignment body back casing, a second orifice formed through said pivot disk, and a third orifice formed through said laser body back casing, and wherein a linear axis of said pivot screw coincides with a first midpoint of said laser body and a second midpoint of said scale alignment body.

2. The medical laser vertical alignment system of claim 1 wherein said front casing of said scale alignment body has a linear alignment slot formed thereon that resides along the linear axis of said scale alignment body, and a moveable stabilizing bar with a locating tab thereon that has a first side that resides adjacent to at least one compression spring with an axis of compression that lies normal to said linear axis of said scale alignment body, and wherein said stabilizing bar has a compression button extending normally therefrom a second side so as to protrude from an opening formed in said scale alignment body casings.

3. The medical laser vertical alignment system of claim 2 further comprising an "L" shaped alignment strip made of a locating tab with a mounting strip extending normally therefrom an edge, wherein said locating tab has a central depression formed thereon and a locating orifice formed there through said depression.

4. The medical laser vertical alignment system of claim 3 wherein said depression and said orifice of said locating tab matingly conform to said stabilizing bar and said locating tab of said scale alignment body.

5. The medical laser vertical alignment system of claim 4 wherein said laser body has:
   two bubble level vials located at diagonally opposite corners of said laser body;
   at least one battery housed in a battery compartment with a battery door;
   a printed circuit board housing a timer circuit, a laser circuit, a timer light, a laser activation button thereon;
   a laser;
   an AC input jack;
   a laser adjustment plate;
   a screw insert; and
   a laser alignment screw;
   that are encased between said back casing and said front casing wherein said casings have posts formed thereon.

6. The medical laser vertical alignment system of claim 5 further comprising a screw insert imbedded in said post adapted to receive and retain said pivot screw.

7. The medical laser vertical alignment system of claim 6 wherein said timer circuit allows said laser to remain on for a predetermined period of time after said laser activation button has been depressed.

8. A medical laser alignment system comprising:
"L" shaped alignment strip adapted for horizontal attachment to a medical device, said alignment strip made of a locating tab with a mounting strip extending normally therefrom an edge, wherein said locating tab has a central depression formed thereon and a locating orifice formed there through said depression;
a scale alignment body enclosed by a first back casing and a first front casing, wherein said front casing of said scale alignment body has a linear alignment slot formed thereon that resides along the linear axis of said scale alignment body, and a stabilizing bar with a locating tab thereon wherein said stabilizing bar and said locating tab are matingly conformed for locking engagement to said central depression and said locating orifice;
a laser body enclosed by a second back casing and a second front casing that house two bubble level vials located at diagonally opposite corners of said laser body, a battery source, a printed circuit board housing a timer circuit and a laser operational circuit, and an adjustable height laser, wherein said second back casing has a second centrally located orifice formed therethrough;
a pivot disk with a first central orifice formed therethrough residing between said laser body's back casing and said scale alignment body's back casing; and
a pivot screw passing through said first, second and third orifices to as to constrain said laser body and said scale alignment body in pivotal connection.

9. The medical laser alignment system of claim 8 wherein a linear axis of said pivot screw coincides with a first midpoint of said laser body and a second midpoint of said scale alignment body.

10. The medical laser alignment system of claim 9 wherein said moveable stabilizing bar has a first side that resides adjacent to at least one compression spring with an axis of compression that lies normal to said linear axis of said scale alignment body, and wherein said stabilizing bar has a compression button extending normally therefrom a second side so as to protrude from an opening formed in said scale alignment body casings.

* * * * *